United States Patent [19]

Morren-De Coster

[11] Patent Number: Plant 5,937

[45] Date of Patent: Apr. 14, 1987

[54] APPLE TREE—JONAGORED

[75] Inventor: Jos Morren-De Coster, Halen, Belgium

[73] Assignee: Daniëlle Gemis-Zuckerman, Davie, Fla.

[21] Appl. No.: 662,978

[22] Filed: Oct. 16, 1984

[51] Int. Cl.[4] ..... A01H 5/03

[52] U.S. Cl. ..... Plt./34

[58] Field of Search ..... Plt./34

[56] References Cited

U.S. PATENT DOCUMENTS

P.P. 5,086 8/1983 Carnefix ..... Plt./34

*Primary Examiner*—Robert E. Bagwill

[57] ABSTRACT

The subject apple tree variety comprises a new Jonagold apple tree (Jonagored) originating as a sport limb mutation of a Jonagold apple tree variety, Jonagold being a crossing of Golden Delicious with Jonathan, bred by New York State Agricultural Experiment station, Geneva, N.Y. The new variety of apple tree is generally similar to its parent with respect to trunk, branches, leaves, flowers and fruit but is uniquely characterized by the significantly large dark-red fruit with most of the apples having white lenticels, and its dark-brown trunk and branches. The new variety is further characterized by the keeping quality of its fruit.

10 Drawing Figures

BACKGROUND AND GENERAL STATEMENT OF THE INVENTION

I discovered my variety of apple tree in my cultivated apple orchard located at Halen, Belgium. I noticed that the top of the Jonagold apple tree was bearing apples colored brown-red. This top and its fruit were unique on the parent tree, and the entire block of trees of Jonagold. Its fruit was already red in the beginning of September, while the rest of the cultivated fruit of Jonagold was still green.

Continued observation of the sport mutation over a period of three weeks indicated that the condition of the fruit remained stable although its color gradually became blood red.

I made cuttings from the sport in question and reproduced them by grafting. I have observed that these characteristics persist already through the second generation. The original sport of the top of my Jonagold apple tree and its descendants have the very same characteristics and fruit color as described above.

THE DRAWINGS

The accompanying drawings illustrate my new Jonagored apple tree and the characteristics of its fruit.

Figure 1:
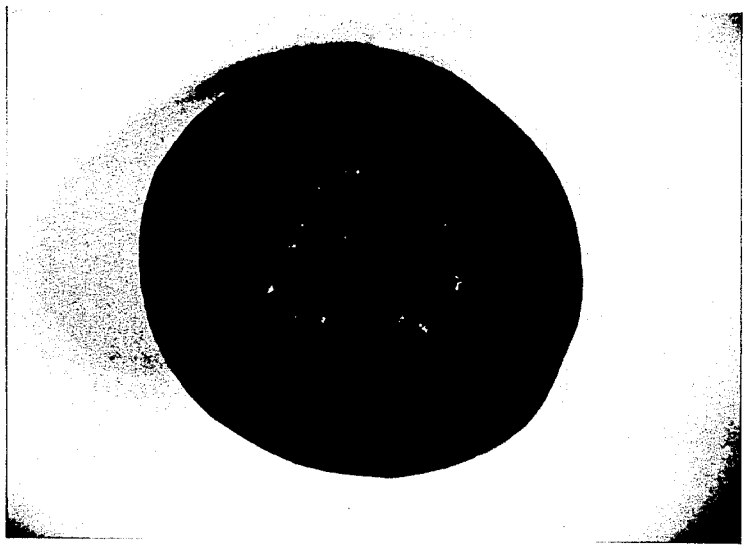
Figure 2:
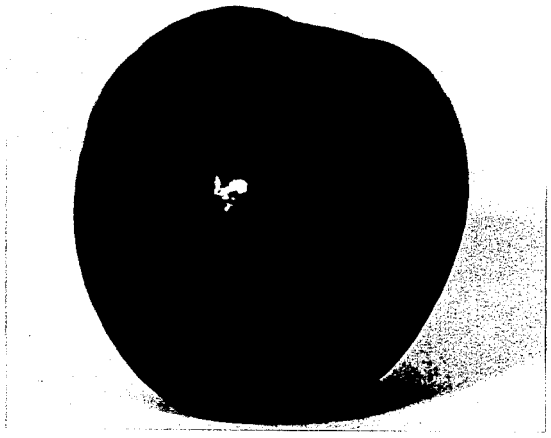
Figure 3:
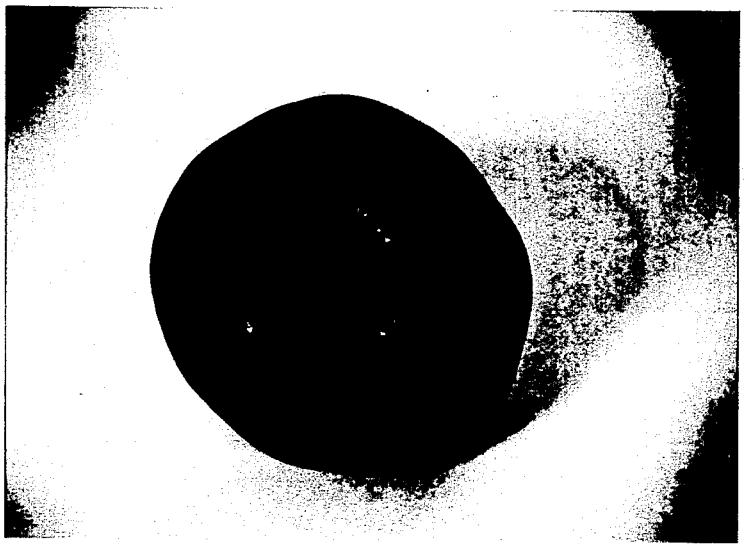

FIGS. 1, 2, 3: This is a photograph of the Jonagored apple; illustrating the complete red color.

FIG. 4: This is a photograph of the parent Jonagored apple tree in its fruit-bearing condition, illustrating its fruit at Sept. 28, 1983.

FIG. 5: This is a trunk of Jonagored tree.

FIG. 6: The leaves and flowers of the Jonagored tree.

Figure 7:
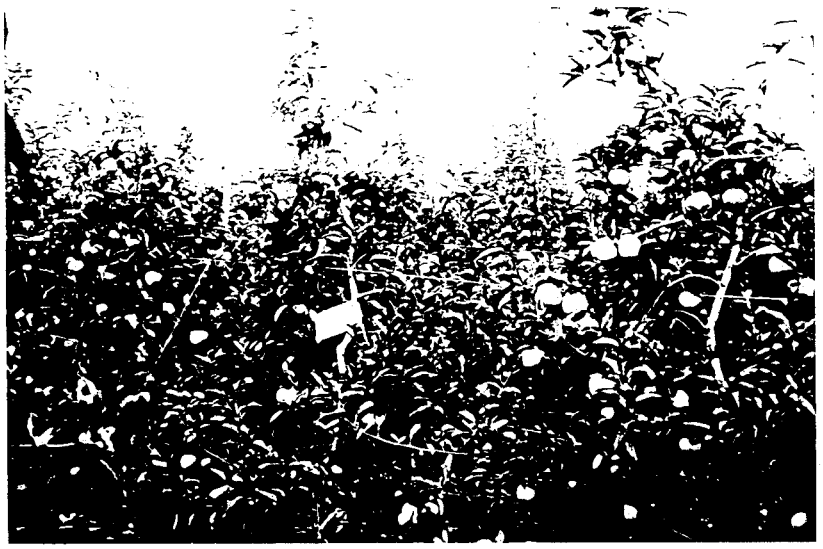

FIG. 7: The parent Jonagold tree between the other Jonagold trees, illustrating the new sport top mutation of my discovery and its fruit at Sept. 12, 1982, as contrasted with the fruit borne by the other limbs of the tree; and the other Jonagold trees.

Figure 8:
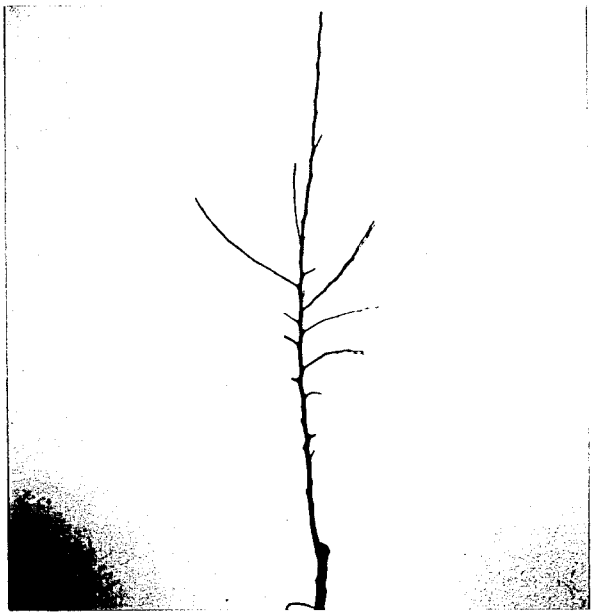

FIG. 8: One year old tree of Jonagored.

Figure 9:
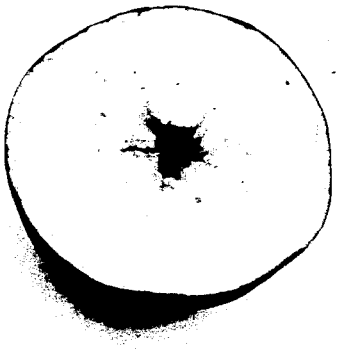
Figure 10:
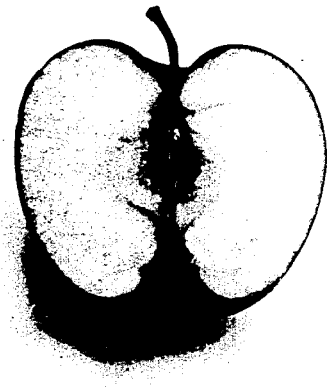

FIGS. 9, 10: Illustrates half of the Jonagored apple.

DESCRIPTION OF THE NEW VARIETY

A detailed description of my new Jonagored apple variety follows, with color terminology being given in accordance with The Royal Horticultural Colour Chart of London. (1938–1940).

Parentage: Sport mutation of Jonagold.

Locality where grown and observed: Halen, Belgium.

Tree: Medium size, vigorous, upright, rapid grower, hardy, very productive, regular bearer.

- *Trunk.*—Stocky, smooth, color is darker than Jonagold, dark brown.
- *Branches.*—Stocky, smooth, relatively few lenticels, medium size lenticels.
- *Leaves.*—Length: 6–8 cm. on May 30th. Width: 5–6 cm. on May 30th. Color: between medium green and dark-green. Size: oval. /The leaves are serrate. /The veins on the back of the leaves are red (Color Chrysanthemum Crimson 824/3.).

Flowers: Time of flowering: Medium. About the end of April, as with Jonagold and Cox Pippin Orange. The pedicels are red. After the flowering, the stamens are against the sepals and are dark-red. The sepals are green with brown-red tips.

Fruit: Specimens described were grown and observed at Halen, Belgium.

- *Date of first and last pickings.*—The end of September and last picking before October 15th.
- *Eating hard ripe.*—September 20th.
- *Size.*—Uniform. Large fruit. Vertical diameter from 7 cm. to 8.5 cm., Horizontal diameter from 6 cm. to 7.5 cm.
- *Form.*—Uniform; Regular; Between round and round-conical.
- *Skin.*—Tough, smooth, glossy, medium thickness. Lenticels: medium, conspicious. The apple is usually brown during the earlier stage of immaturity, while the apple becomes blood red at maturity. Color: Ground color: yellow. Color markings: basically from near Currant Red 821 to near Cardinal Red 822.
- *Seeds.*—5–8 perfect; not over 2 per cell. Length 1 cm. Breadth: ½ cm. Form: acute. Color: Chestnut, auburn.

*Flesh.*—Juicy, color: white with a yellowish tint. Texture: firm, fine, crisp. Flavor: sweet/sour. Quality: very high.

*Core.*—Core-line: absent. Cross-section: cells are closed.

*Stem.*—Thickness of the stem: slender. Length of stem: very long — from 2.5 cm. to 4 cm.

*Cavity.*—Symmetrical. Depth — from 1.5 to 1.25 cm. Breadth: from 2 cm. to 2.5 cm.

*Basin.*—Symmetrical; 5 crowned, crowns prominent. Depth: from 1 cm. to 1.5 cm.

*Use.*—Dessert, culinary, juice; primarily for dessert.

*Keeping quality.*—Natural: Good: up to 7 months in ordinary storage. Artificial: keeps very good (as well as Golden Delicious).

*Resistance to insects and diseases.*—No unusual susceptibility noted.

I claim:

1. A new and distinct variety of fruiting apple tree Malus Mill-type, as described and illustrated, characterized by a vigorous, upright growth habit with large dark-red fruit and most with white lenticels, by the keeping quality of its fruit, the wood of the tree being darker than Jonagold, and the growth habit being the same as Jonagold.

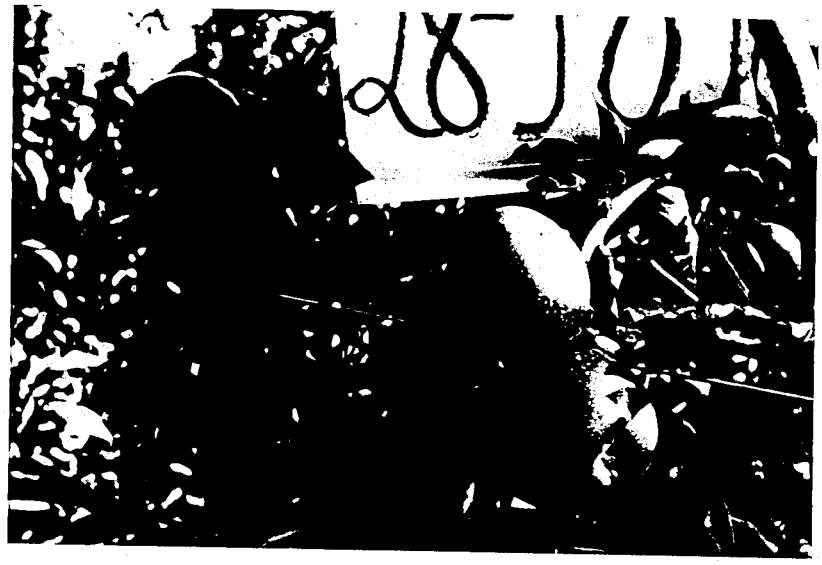
FIG. 4
FIG. 5
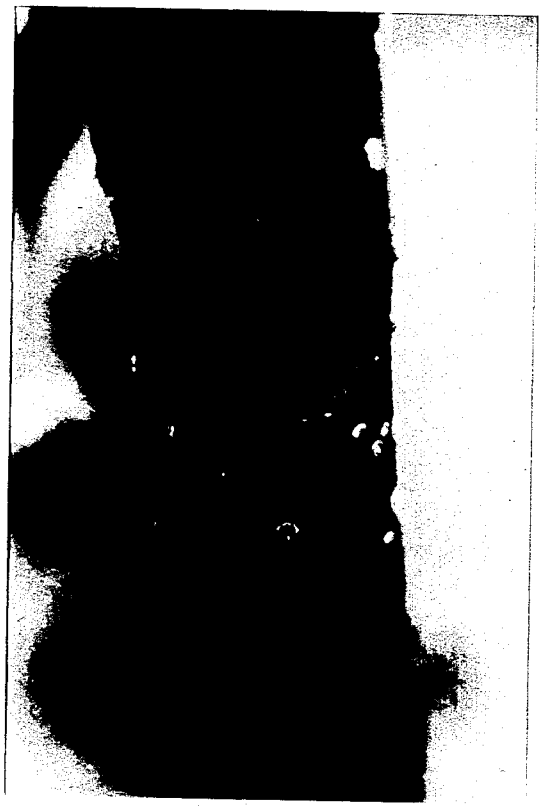
FIG. 6
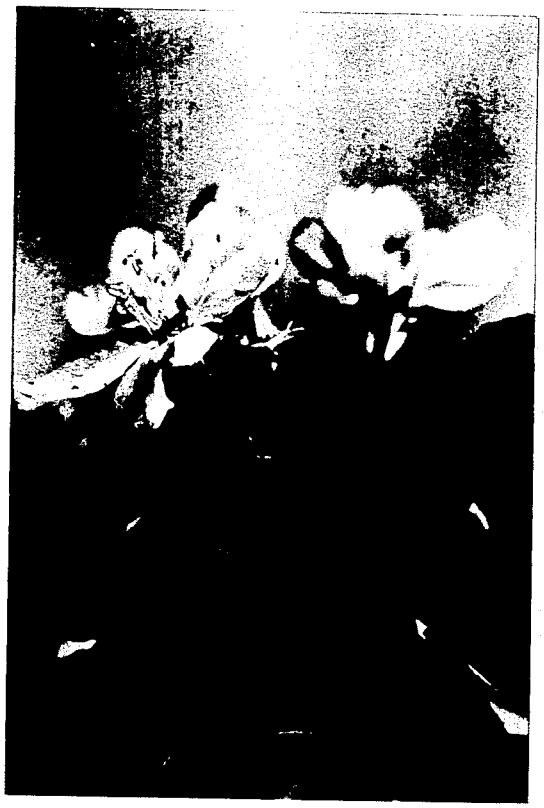

* * * * *